(12) United States Patent
Grünzig

(10) Patent No.: US 9,891,039 B1
(45) Date of Patent: Feb. 13, 2018

(54) METHOD AND DEVICE FOR MEASURING PLATING RING ASSEMBLY DIMENSIONS

(71) Applicant: GLOBALFOUNDRIES Inc., Grand Cayman (KY)

(72) Inventor: Sven Heiko Grünzig, Dresden (DE)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 15/458,124

(22) Filed: Mar. 14, 2017

(51) Int. Cl.
*G01B 11/14* (2006.01)
*G01B 11/00* (2006.01)
*G01N 21/95* (2006.01)
*G01N 21/88* (2006.01)

(52) U.S. Cl.
CPC ........ *G01B 11/002* (2013.01); *G01N 21/8806* (2013.01); *G01N 21/9501* (2013.01); *G01N 2201/06113* (2013.01)

(58) Field of Classification Search
CPC .............................. G01B 11/14; G01B 11/002
USPC ........................................................ 356/625
See application file for complete search history.

(56) References Cited

U.S. PATENT DOCUMENTS 6,080,291 A * 6/2000 Woodruff ............. C25D 17/001
204/212
8,968,531 B2 3/2015 Wilson et al.

* cited by examiner

*Primary Examiner* — Roy M Punnoose
(74) *Attorney, Agent, or Firm* — Ditthavong & Steiner, P.C.

(57) ABSTRACT

A method for obtaining distance measurements for a plating ring assembly and related device are provided. Embodiments include attaching a measurement device to a plating ring assembly, the plating ring assembly including: an outer ring, wherein the measurement device is attached to the outer ring and configured to rotate along the outer ring, a seal extending from a bottom surface of the outer ring along a circumference of the plating ring assembly, contact fingers located along the circumference of the plating ring assembly, between the outer ring and the seal, rotating the measurement device along the circumference of the outer ring by rotating the measurement device or the plating ring assembly; and obtaining critical dimensions of and between the seal and contact fingers with the measurement device.

20 Claims, 3 Drawing Sheets

METHOD AND DEVICE FOR MEASURING PLATING RING ASSEMBLY DIMENSIONS

TECHNICAL FIELD

The present disclosure relates to semiconductor workpiece processing. In particular, the present disclosure relates to dimension tolerance measurements of a plating ring assembly.

BACKGROUND

Semiconductor devices are generally fabricated on substrates using different machines, including an electroplating processor that plates layers of conductive materials onto a work piece, such as a semiconductor wafer or substrate. Existing electroplating processors use a contact ring having contact fingers that make electrical connections to the surface of the substrate. A shield can be used to partially overlay the contact fingers to change the electric field around the outer edge of the workpiece and contact fingers to reduce or eliminate non-uniform plating problems. Manual inspections can be performed to visually check a gap between the contact finger height and a reference. The inspection is performed outside of the equipment after the ring assembly is removed. A dynamometer can be manually applied individually to each contact finger, which is a time consuming process.

Plating defects are mainly caused by sealing and contact finger problems. To date, there has been no reliable or accurate method for early detection of these root causes of plating defects. A need therefore exists for methodology and a device enabling early detection of sealing and contact finger problems on plating ring assemblies.

SUMMARY

An aspect of the present disclosure is to provide a fast, easy to use, and fail-safe method of determining critical dimensions on a plating ring assembly. Early detection of sealing and contact finger problems can avoid plating defects. Quality inspection checks of new or refurbished plating ring assemblies can be performed. In addition, a tolerance check can be performed during preventive or corrective maintenance performed on the plating ring assemblies. With the present disclosure, dimension tolerances can be detected with a measurement fixture device having an optical sensor.

Additional aspects and other features of the present disclosure will be set forth in the description which follows and in part will be apparent to those having ordinary skill in the art upon examination of the following or may be learned from the practice of the present disclosure. The advantages of the present disclosure may be realized and obtained as particularly pointed out in the appended claims.

According to the present disclosure, some technical effects may be achieved in part by a method including attaching a measurement device to a plating ring assembly, the plating ring assembly including: an outer ring, wherein the measurement device is attached to the outer ring and configured to rotate along the outer ring, a seal extending from a bottom surface of the outer ring along a circumference of the plating ring assembly, contact fingers located along the circumference of the plating ring assembly, between the outer ring and the seal, rotating the measurement device along the circumference of the outer ring by rotating the measurement device itself or by rotating of the plating ring assembly; and obtaining critical dimensions of and between the seal and contact fingers with the measurement device.

Aspects of the present disclosure include processing the critical dimensions obtained by the measuring device with a programmed processor. Other aspects include processing the critical dimensions with the programmed processor located on the measuring device. Yet other aspects include processing the critical dimensions with the programmed processor remotely located from the measuring device. Additional aspects include rotating the measurement device or plating ring assembly at least 360° along the circumference of the outer ring. Another aspect includes between or during the rotation of the measurement device or ring assembly, changing the position of the measuring device back and forth between the seal and contact fingers and recording of position changes An additional aspect includes obtaining the critical dimensions with an optical sensor of the measurement device. Other aspects include the critical dimensions including z-axis and y-axis distances of and between the seal and the contact fingers. In certain aspects the optical sensor is selected from a laser spot sensor, laser profile sensor or a confocal sensor.

Another aspect of the present disclosure is device including: a plating ring assembly including: an outer ring, a seal extending from a bottom surface of the outer ring along a circumference of the plating ring assembly, contact fingers located along the circumference of the plating ring assembly, between the outer ring and the seal; and a measurement device attached to the outer ring, wherein the measurement device is configured to rotate along a circumference of the outer ring of the plating ring assembly, or the plating ring assembly is configured to rotate while the measurement device is stationary, and wherein the measurement device is configured to obtain critical dimensions of and between the seal and contact fingers.

Aspects include a programmed processor for processing the critical dimensions obtained by the measuring device, the programmed processor located on the measuring device. Other aspects include a programmed processor for processing the critical dimensions obtained by the measuring device, the programmed processor located remotely from the measuring device. Additional aspects include the measurement device being configured to rotate at least 360° along the circumference of the outer ring. Other aspects include the measurement device being configured to change position back and forth between the seal and contact fingers between or during rotation of the measurement device, or between or during the rotation of the plating ring assembly with a stepping motor. Yet other aspects include the measurement device including an optical sensor for obtaining the critical dimensions. Further aspects include the critical dimensions including z-axis and y-axis distances of and between the seal and the contact fingers. Additional aspects include the optical sensor being selected from a laser spot sensor, laser profile sensor or a confocal sensor.

Yet another aspect of the present disclosure includes a method attaching a measurement device comprising an optical sensor to a plating ring assembly, the plating ring assembly including: an outer ring, wherein the measurement device is attached to the outer ring and configured to rotate along the outer ring, a seal extending from a bottom surface of the outer ring along a circumference of the plating ring assembly, contact fingers located along the circumference of the plating ring assembly, between the outer ring and the seal, rotating the measurement device or rotating the plating ring assembly along the circumference of the outer ring;

changing a position of the measurement device back and forth between the seal and contact fingers between or during rotation of the measurement device, or between or during rotation of the plating ring assembly with a stepping motor; obtaining critical dimensions of and between the seal and contact fingers with the optical sensor of the measurement device; and processing the critical dimensions obtained by the measuring device, and processing of data of the stepping motor with a programmed processor.

Aspects include the critical dimensions including z-axis and y-axis distances of and between the seal and the contact fingers. Other aspects include the optical sensor being selected from a laser spot sensor, laser profile sensor or a confocal sensor.

Additional aspects and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about."

The present disclosure addresses and solves the current problem of plating defects arising from sealing and contact finger problems occurring on new or refurbished plating ring assemblies caused by a changing of their mechanical tolerances during their lifetime. Methodology in accordance with embodiments of the present disclosure includes checking plating ring assemblies having a seal ring and contact fingers for their dimension tolerances by a measurement fixture device having an optical sensor.

Still other aspects, features, and technical effects will be readily apparent to those skilled in this art from the following detailed description, wherein preferred embodiments are shown and described, simply by way of illustration of the best mode contemplated. The disclosure is capable of other and different embodiments, and its several details are capable of modifications in various obvious respects. Accordingly, the drawings and description are to be regarded as illustrative in nature, and not as restrictive.

Figure 1:
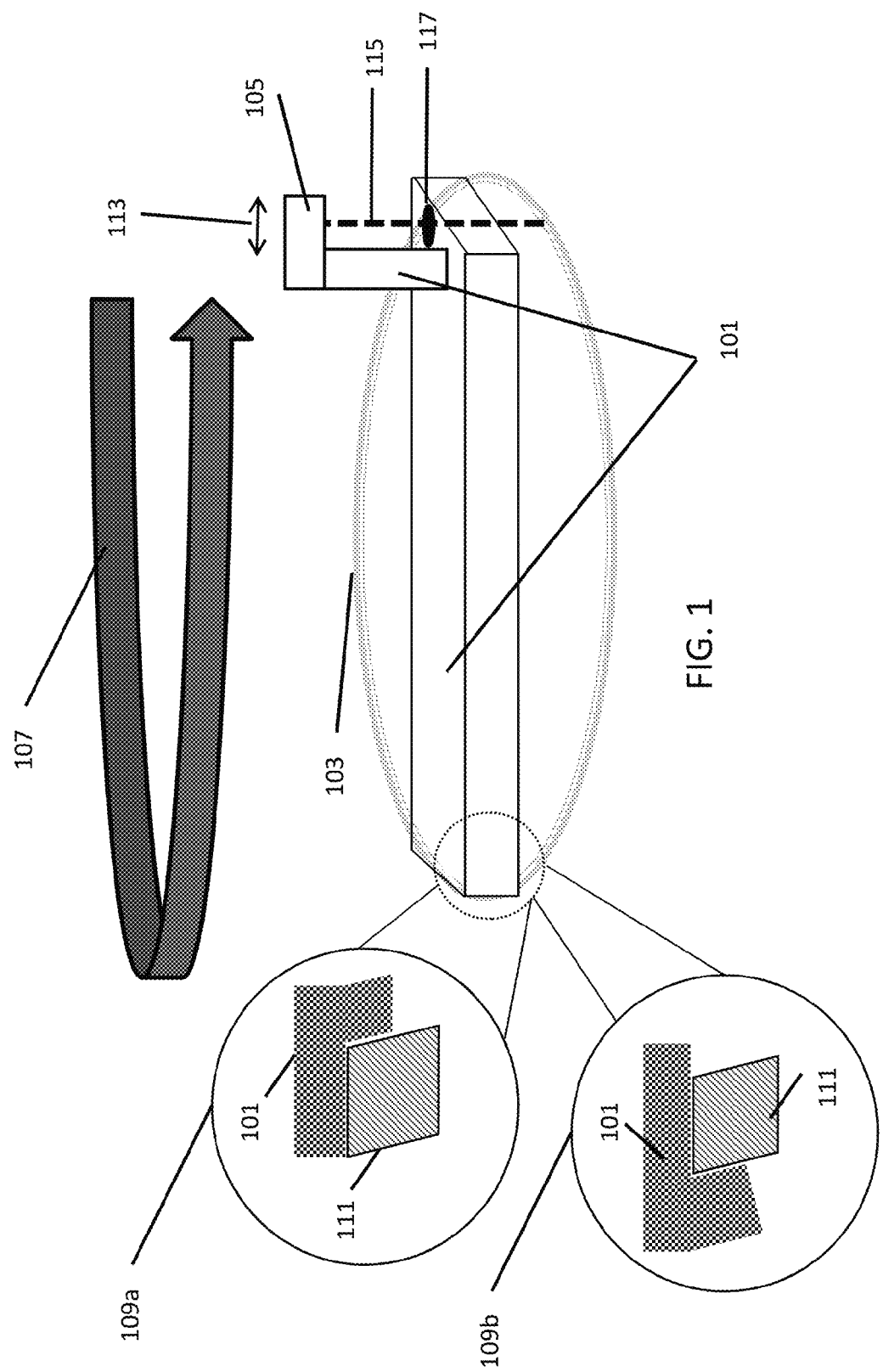
FIG. 1 illustrates a measurement device mounted to an underlying plating ring assembly, in accordance with an exemplary embodiment.

FIG. 1 illustrates a measurement device 101 mounted on top of a plating ring assembly 103. The measurement device 101 includes a optical sensor 105. Examples of an optical sensor, which can include light or laser sensors, for distance measurements include a laser spot sensor, laser profile sensor or a confocal sensor. The resolution of the profile sensor (Y-axis) can be 50 µm or 0.05 mm.

The measurement device 101 is manually mounted to the plating ring assembly 103 and designed to rotate along the circumference of the plating ring assembly 103 by rotating the measurement device itself, or by rotating of the plating ring assembly 103 under a stationary measurement device 101. A circular workpiece or the wafer is mounted to the plating ring assembly 103 during the plating process. The measurement device 101 can be used before or after the plating process. Therefore, the plating ring assembly 103 does not contain a wafer or workpiece during the measuring by the measurement device 101. The measurement device 101 can be equipped with sensors having a resolution accuracy of 0.1 µm. Other sensors can have a resolution accuracy of 0.02 mm or 20 µm.

As shown by directional arrow 107, the measuring device 101 rotates at least 360° around the circumference of the outer ring 111. The measurement device 101 can rotate along the circumference of the outer ring 111 by being actively driven with a motor, or in a stationary manner way if the plating ring assembly 103 is rotating under a stationary measurement device 101. In either case, the measurement device 101 rotates along the circumference of the outer ring 111.

Figure 3:
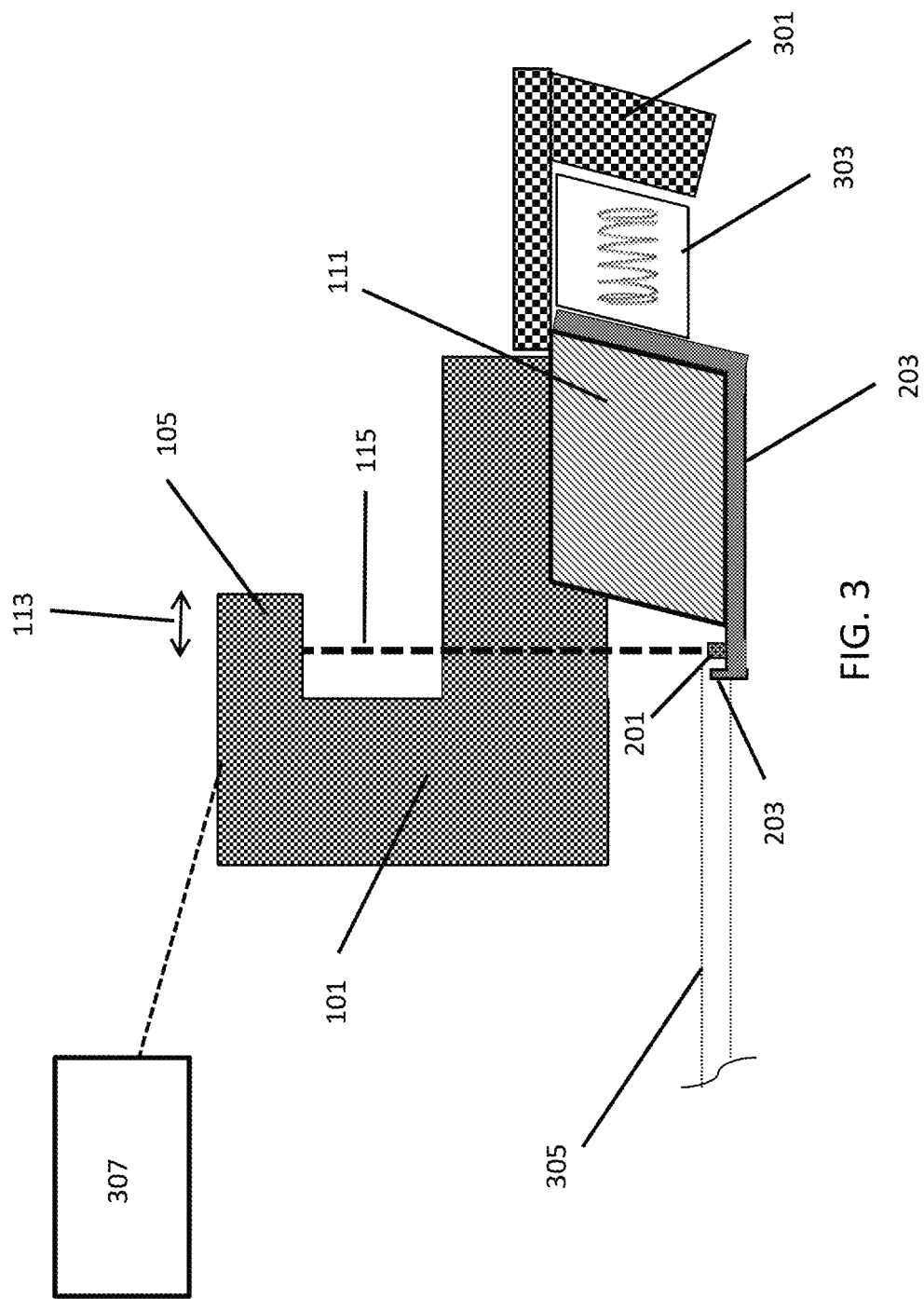
FIG. 3 illustrates, in cross sectional view, the measurement device mounted to an outer ring of the plating ring assembly of FIG. 1, in accordance with an exemplary embodiment.

Enlarged regions 109a and 109b illustrate examples in which the measurement device 101 is mounted on an outer ring 111 of the plating ring assembly 103. As shown in FIG. 3, a bottom surface of measurement device 101 is adapted with a clamp 301 to the shape of the outer ring 111 on an inner and/or outer side of the outer ring 111 such that it is fixedly secured and capable of moving along the entire circumference of the outer ring 111. The outer side of the clamp 301 contains a spring 303 to apply a gentle force to the clamp 301 during the movement to eliminate a movement of the measurement device 101 in Y-axis direction and to avoid an overly tight contact of a shoe of the clamp 301 to the plating ring assembly 103, which would avoid a smooth movement of the measurement device 101.

The measurement device 101 is also shape-adapt mounted on the opposite outer and/or inner side of the plating ring assembly 103 depending on the design of the plating ring assembly 103 which might not allow a movement with a mounted inner ring clamp shoe, but only with an outer ring clamp shoe. In this instance, only an outer clamp 301 would be used, which is illustrated in further detail in FIG. 3. It is beneficial to adapt the shape of a shoe of the clamp 301 to the exact shape of the ring assembly 103 to avoid the creation of measurement tolerances by the gap which is an unstable position during movement. In addition with the spring 303 in the outer clamp (located on the side where the optical sensor 105 is fixed on the measurement device 101) the optical sensor 105 position is stable during rotation. The rotation of the measurement device 101 along the circumference of the outer ring 111, or the rotation of the plating ring assembly 103, can be mechanically driven with a motor or manually operated by a human.

The optical sensor 105 is configured to move back and forth along a Y-axis represented by bi-directional arrow 113. The optical sensor 105 emits a light 115 downward through an optional opening 117, or alternatively along side of the measurement device 101 down to the plating ring assembly 103. The optical distance sensor 105 is configured to move back and forth between contact fingers and a seal of the plating ring assembly 103, described in further detail in FIGS. 2 and 3.

Figure 2:
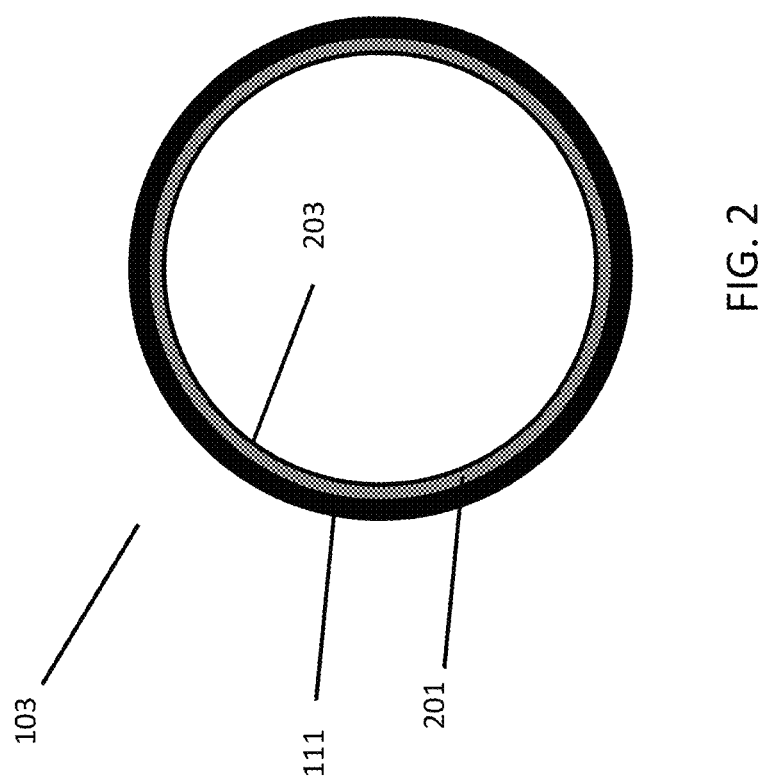
FIG. 2 illustrates, in top view, the plating ring assembly as shown in FIG. 1.

FIG. 2 is a top view of the plating ring assembly 103. The top view of the plating ring assembly 103 shows outer ring 111 and contact fingers 201 which extend around the circumference of the plating ring assembly 103 inside the circumference of the outer ring assembly 111. Each contact finger 201 is spaced apart from an adjacent contact finger 201 and is a finger-shaped structure that comes into contact with an upper surface of a wafer or workpiece (FIG. 3) positioned in the plating ring assembly 103. Seal 203 is ring shaped and extends along an outer side and a bottom surface of the outer ring 111, under the contact fingers 201, and contacting a lower surface of a workpiece or wafer (FIG. 3) positioned on the plating ring assembly 103. Seal 203 can be composed of a polymer/plastic material.

By collecting the positions and associated signals of the optical sensor 105, the horizontal critical dimensions (Y-axis) can be calculated in addition to the processing of the Z-axis signals if required. In this example, a defined motor-driven movement of optical sensor 105 would be applied. The processing of the positions can be applied by way of a stepping motor. The accuracy of the driving position of the stepping motor is within a range of +/−50 micrometers (μm) or +/−0.05 millimeter (mm). The axis data collection is a measurement of the optical sensor 105, with the determination of the Y-axis values (gap between the seal and the finger, also possible to calculate the so called "centering" of the seal and ring overlay of both radii centers) is a non-direct measurement by calculating the stepping motor pulses and the ratio of one step related to one millimeter. The accuracy of such a stepping motor is usually around 50 μm or 0.05 mm (millimeter) which is sufficient to calculate the gap between seal and contact finger.

FIG. 3 illustrates the measurement device 101 mounted to the outer ring 111. Wafer or workpiece 305 is shown only as a reference point. The wafer or workpiece 305, is mounted to the plating ring assembly during the plating process. The measurement device 101 can be used before or after the plating process takes place. Therefore, plating ring assembly 103 itself does not contain the wafer or workpiece 305 during the measurement by the measuring device 101.

The optical sensor 105 is configured to emit light as the measurement device 101 rotates 360° around the outer ring 111 by rotating the measurement device 101 itself or by rotating of the plating ring assembly 103. The measurement device 101 can be moved side-to-side between the seal 203 and the contact fingers 201 at a stopped theta movement to check that the horizontal distance between seal 203 and the contact fingers 201 is within the required tolerance. Based on this Y-axis movement, data collection can be carried out for rotations with different radii or for fixed theta positions with the full scan of the horizontal distance between seal 203 and the contact fingers 201. The measurement device 101 can operate with a stepping motor for the change of the Y-axis position of the sensor. In this case the measurement device 101 includes the stepping motor and enables the determination of the critical distances of the seal, the finger, and distances between seal and finger, by using a calculation of the stepping motor linear distance according to the steps the motor has moved.

Movement between seal 203 and contact fingers 201 leads to information about the height of the seal 203 and the height of the contact fingers 201 which can be recorded. The information about the movement is describing the gap between the seal and the finger which is also a critical dimension to avoid defects during the plating process. Without recording the position data (e.g. manually carried out movement) the information is lost.

The distance data acquired by the measurement device 101 is processed by a programmed processor 307 which can be contained within the measuring device 101 or remotely located from the measurement device 101 and wired or wirelessly connected. Critical dimensions measured at the contact fingers 201 and seal 203 can be processed to determine if any distances are outside a tolerance range and therefore likely to cause plating errors during plating processing of the workpiece or wafer 305.

The programmed processor 307 can include personal computers (PCs) or the like. Such devices are intended to represent a general class of data processing device commonly used to run client software and various end-user applications. The hardware of such personal computer platforms typically is general purpose in nature, albeit with an appropriate network connection for communication via the intranet, the Internet and/or other data networks. As known in the data processing and communications arts, each such general-purpose personal computer typically includes a central processor, an internal communication bus, various types of memory (RAM, ROM, EEPROM, cache memory, etc.), disk drives or other code and data storage systems, and one or more network interface cards or ports for communication purposes. Of course, a personal computer or other end user data device will also have or be coupled to a display and one or more user input devices such as alphanumeric and other keys of a keyboard, a mouse, a trackball, etc. The display and user input element(s) together form a user interface, for interactive control of the computer and through the computer to control other mail processing operations. These user interface elements may be locally coupled to the computer, for example in a workstation configuration, or the user interface elements may be remote from the computer and communicate therewith via a network. The hardware elements, operating systems and programming languages of such end user data devices are conventional in nature, and it is presumed that those skilled in the art are adequately familiar therewith.

The embodiments of the present disclosure can achieve several technical effects, including early detection of critical dimensions of seal and contact fingers of new or refurbished plating ring assemblies, thereby effectively improving device reliability, reducing plating defects and reducing overall costs. The present disclosure enjoys industrial applicability in any of various industrial applications, e.g., microprocessors, smart phones, mobile phones, cellular handsets, set-top boxes, DVD recorders and players, automotive navigation, printers and peripherals, networking and telecom equipment, gaming systems, and digital cameras. The present disclosure therefore enjoys industrial applicability in any of various types of plating devices that process semiconductor wafers or workpieces, particularly in the 20 nanometer (nm) technology node and beyond.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. A method comprising:
    attaching a measurement device to a plating ring assembly, the plating ring assembly including:
        an outer ring, wherein the measurement device is attached to the outer ring and configured to rotate along the outer ring,
        a seal extending from a bottom surface of the outer ring along a circumference of the plating ring assembly,
        contact fingers located along the circumference of the plating ring assembly, between the outer ring and the seal,
    rotating the measurement device along the circumference of the outer ring by rotating the measurement device or the plating ring assembly; and
    obtaining critical dimensions of and between the seal and contact fingers with the measurement device.

2. The method according to claim 1, further comprising:
    processing the critical dimensions obtained by the measuring device with a programmed processor.

3. The method according to claim 2, comprising:
    processing the critical dimensions with the programmed processor located on the measuring device.

4. The method according to claim 2, comprising:
    processing the critical dimensions with the programmed processor remotely located from the measuring device.

5. The method according to claim 1, comprising:
    rotating the measurement device or plating ring assembly at least 360° along the circumference of the outer ring.

6. The method according to claim 5, further comprising:
    between or during the rotation of the measurement device or ring assembly, changing the position of the measuring device back and forth between the seal and contact fingers with a stepping motor, and recording of position changes.

7. The method according to claim 1, comprising:
    obtaining the critical dimensions with an optical sensor of the measurement device.

8. The method according to claim 7, wherein the critical dimensions include z-axis and y-axis distances of and between the seal and the contact fingers.

9. The method according to claim 6, wherein the optical sensor is selected from a laser spot sensor, laser profile sensor or a confocal sensor.

10. A device comprising:
    a plating ring assembly comprising:
        an outer ring,
        a seal extending from a bottom surface of the outer ring along a circumference of the plating ring assembly,
        contact fingers located along the circumference of the plating ring assembly, between the outer ring and the seal; and
    a measurement device attached to the outer ring,
    wherein the measurement device is configured to rotate along a circumference of the outer ring of the plating ring assembly, or the plating ring assembly is configured to rotate while the measurement device is stationary, and
    wherein the measurement device is configured to obtain critical dimensions of and between the seal and contact fingers.

11. The device according to claim 10, further comprising:
    a programmed processor for processing the critical dimensions obtained by the measuring device, the programmed processor located on the measuring device.

12. The device according to claim 10, further comprising:
    a programmed processor for processing the critical dimensions obtained by the measuring device, the programmed processor located remotely from the measuring device.

13. The device according to claim 10, wherein the measurement device is configured to rotate at least 360° along the circumference of the outer ring.

14. The device according to claim 10, wherein the measurement device is configured to change position back and forth between the seal and contact fingers between or during rotation of the measurement device, or between or during the rotation of the plating ring assembly with a stepping motor.

15. The device according to claim 10, wherein the measurement device comprises an optical sensor for obtaining the critical dimensions.

16. The method according to claim 15, wherein the critical dimensions include z-axis and y-axis distances of and between the seal and the contact fingers.

17. The method according to claim 15, wherein the optical sensor is selected from a laser spot sensor, laser profile sensor or a confocal sensor.

18. A method comprising:
    attaching a measurement device comprising an optical sensor to a plating ring assembly, the plating ring assembly including:
        an outer ring, wherein the measurement device is attached to the outer ring and configured to rotate along the outer ring,
        a seal extending from a bottom surface of the outer ring along a circumference of the plating ring assembly,
        contact fingers located along the circumference of the plating ring assembly, between the outer ring and the seal,
    rotating the measurement device along the circumference of the outer ring;
    changing a position of the measurement device back and forth between the seal and contact fingers between or during rotation of the measurement device, or between or during rotation of the plating ring assembly with a stepping motor;
    obtaining critical dimensions of and between the seal and contact fingers with the optical sensor of the measurement device; and
    processing the critical dimensions obtained by the measuring device, and processing of data of the stepping motor with a programmed processor.

19. The method according to claim 18, wherein the critical dimensions include z-axis and y-axis distances of and between the seal and the contact fingers.

20. The method according to claim 19, wherein the optical sensor is selected from a laser spot sensor, laser profile sensor or a confocal sensor.

* * * * *